United States Patent [19]

Schatz

[11] 4,227,530
[45] Oct. 14, 1980

[54] METHOD OF EMPLOYING RECLOSABLE FASTENER TAPE SYSTEM

[75] Inventor: Clarence H. Schatz, West Chester, Pa.

[73] Assignee: Scott Paper Company, Philadelphia, Pa.

[21] Appl. No.: 828,755

[22] Filed: Aug. 29, 1977

Related U.S. Application Data

[63] Continuation-in-part of Ser. No. 724,983, Sep. 20, 1976, abandoned.

[51] Int. Cl.³ .............................................. A61F 13/16
[52] U.S. Cl. ............................ 128/287; 128/DIG. 30
[58] Field of Search ............... 128/284, 287, DIG. 15, 128/290 R, DIG. 30

[56] References Cited

U.S. PATENT DOCUMENTS

| | | | |
|---|---|---|---|
| 3,616,114 | 10/1971 | Hamaguchi | 128/DIG. 30 |
| 3,794,838 | 2/1974 | Buell | 128/287 |
| 3,833,456 | 9/1974 | Reed et al. | 128/287 |
| 3,848,594 | 11/1974 | Buell | 128/287 |
| 3,987,793 | 10/1976 | Milnamow | 128/287 |
| 3,999,545 | 12/1976 | Milnamow | 128/284 |
| 3,999,546 | 12/1976 | Feldman et al. | 128/287 |
| 4,020,842 | 5/1977 | Richman et al. | 128/287 |
| 4,034,752 | 7/1977 | Tritsch | 128/287 |
| 4,044,767 | 8/1977 | Tritsch | 128/287 |
| 4,049,001 | 9/1977 | Tritsch | 128/287 |
| 4,050,121 | 9/1977 | Richman | 128/287 |
| 4,067,338 | 1/1978 | Van Vliet | 128/287 |

Primary Examiner—Robert W. Michell
Assistant Examiner—C. W. Shedd
Attorney, Agent, or Firm—Martin L. Faigus; William J. Foley

[57] ABSTRACT

A reclosable fastener tape system adaptable for use in connecting together segments of a garment includes a release strip and an adhesive tape fastener. The release strip has an adhesive layer on one of its surfaces that is directly attachable to the garment, and the fastener has first and second tape sections adhered to the opposite surface of the release strip through an adhesive surface-release surface interface. The release strip and adhesive tape fastener are the only adhesive containing substrates of the tape system when the system is attached to the garment.

In accordance with a method of this invention the fastener tape system is attached to the garment, and thereafter the adhesive surface of the first tape section is attached to a segment of the garment that is different from the segment to which the second tape section is attached to thereby connect these segments together. Thereafter, if it is desired to adjust or modify the fit of the garment on the wearer, or merely open the garment to inspect it, as may be desirable when the garment is a disposable diaper, it is only necessary to detach the second tape section from the garment at the adhesive surface-release surface interface.

4 Claims, 6 Drawing Figures

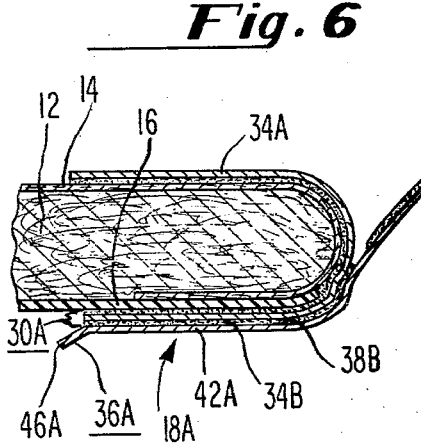
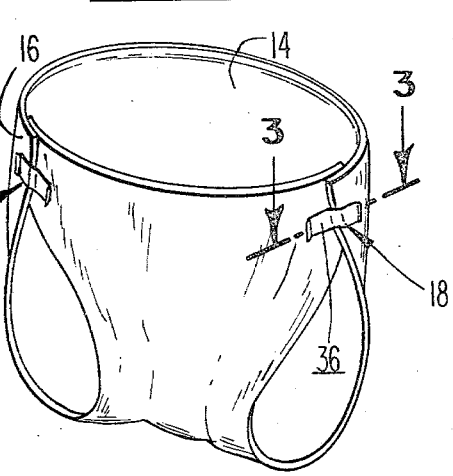
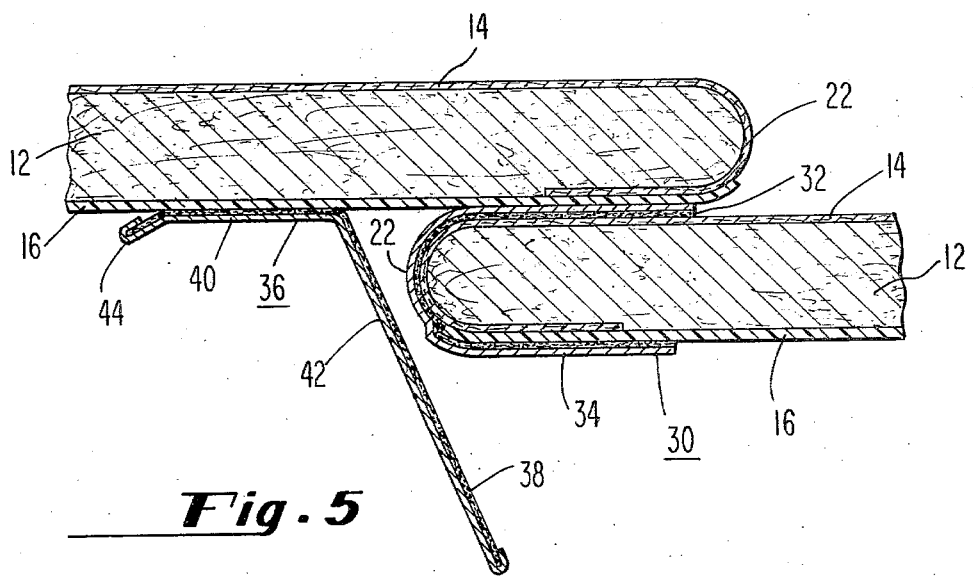

METHOD OF EMPLOYING RECLOSABLE FASTENER TAPE SYSTEM

RELATED APPLICATION

This application is a continuation-in-part of U.S. Application Ser. No. 724,983, filed Sept. 20, 1976, now abandoned.

BACKGOUND OF THE INVENTION

1. Field of the Invention

This invention relates to a fastener tape system for use in connecting segments of a garment together, and more specifically, to a fastener tape system including an adhesive tape fastener which can be employed to reconnect the segments together after they have initially been opened. The invention also relates to a method of employing the system.

2. Description of the Prior Art

Pressure-sensitive adhesive tapes are very useful in providing a quick, easy and economical means of connecting segments of a garment together. These tapes are particularly beneficial for connecting together segments of disposable garments, such as bibs, diapers, hospital gowns, etc. It is often desirable to reopen these garments to either inspect them or adjust their fit. Reopening the garments is accomplished by separating a section of the tape from a segment of the garment; an operation that often destroys the tackiness of the tape, or either tears the tape or garment. This makes refastening the tape difficult or impossible.

U.S. Pat. No. 3,848,596, discloses a fastener tape system which permits refastening of an adhesive tape after it has initally been peeled from a diaper. The end portion of the tape, which is adapted to be peeled from the diaper, has a pressure sensitive adhesive surface which initially is covered by two, separate protective strips. Each protective strip is adhered to a different area of the adhesive surface, and only one of the strips is removed to permit the tape to be intially adhered to the diaper. The other protective strip is removed to expose a fresh adhesive area after the end portion of the tape has been opened. The tape can then be resealed through its fresh adhesive area. This particular system is somewhat complex in design, and also requires the separate disposal of the protective strips after they have been removed from the tape. It has long been recognized that these protective strips present a safety hazard to infants. Specifically, if a strip is not properly disposed of an infant may ingest it, and possibly choke to death. To eliminate this safety hazard "linerless" tape fastener systems have been developed, e.g., systems in which a release liner remains fixed to the diaper (or any other garment) after a portion of the tape protected by said liner has been opened for use. A linerless, reclosable system is described in U.S. Pat. No. 4,020,842, issued to Richman et al. This system is somewhat complex; requiring three distinct adhesive tape substrates laminated together. Thus, the fastening art is in need of a simple and economical reclosable tape fastener system that preferably is linerless. It is to such a system, and its method of use, that the instant invention is directed.

SUMMARY OF THE INVENTION

A reclosable fastener tape system for use in connecting together segments of a garment includes an adhesive tape fastener divided into two tape sections. One tape section is adapted to be connected to a first segment of a garment, adjacent an edge thereof, through a release surface-adhesive surface interface. When this tape section is connected to the first segment, the other tape section can be extended beyond the edge for permanent attachment to a second segment of the garment. When it is desired to reopen the first and second garment segments, after they have been initially connected together, a user need only separate the one tape section from the first garment segment at the release surface-adhesive surface interface. Because of this interface, the adhesive surface will not be damaged, and therefore the tape fastener can be reclosed by adhesively reattaching the one tape section to the first garment segment.

In the most preferred embodiment of this invention the fastener tape system is linerless; with the two tape sections of the system, prior to use, being adhered to surfaces of the garment through release surface-adhesive surface interfaces. Most preferably these release surfaces are provided by one side of a release strip. The other side of the release strip includes an adhesive layer to adhere the strip to the garment with the release surfaces facing outwardly to receive the adhesive surfaces of the first and second tape sections. The release strip and adhesive tape fastener are the only adhesive-containing substrates of the tape system when it is attached to the garment.

Other objects and advantages of this invention will become apparent upon referring to the detailed description which follows, taken in conjunction with the drawings.

BRIEF DESCRIPTION OF THE DRAWING

FIG. 3 is an enlarged sectional view along line 3—3 of FIG. 4, showing the fastener tape system of FIG. 1 in position for retaining the disposable diaper about the torso of a wearer;

FIG. 4 is an isometric view of the diaper showing the general configuration it assumes when secured about the torso of a wearer;

FIG. 5 is an enlarged sectional view similar to FIG. 4, but showing the fastener tape system in a condition for permitting removal or adjustment of the disposable diaper; and FIG. 6 is a sectional view of a second embodiment of a tape system in accordance with this invention showing a tape section in position for initially securing a diaper about the torso of a wearer.

DESCRIPTION OF THE PREFERRED EMBODIMENTS OF THE INVENTION

The fastener tape systems of this invention can be employed to secure together segments of various different garments. These systems are believed to be most beneficially used with single or limited use garments such as disposable diapers, bibs, hospital gowns and the like. For purpose of description, the fastener tape systems of this invention will be described in connection with their use with disposable diapers, the most preferred use to date.

Figure 1:
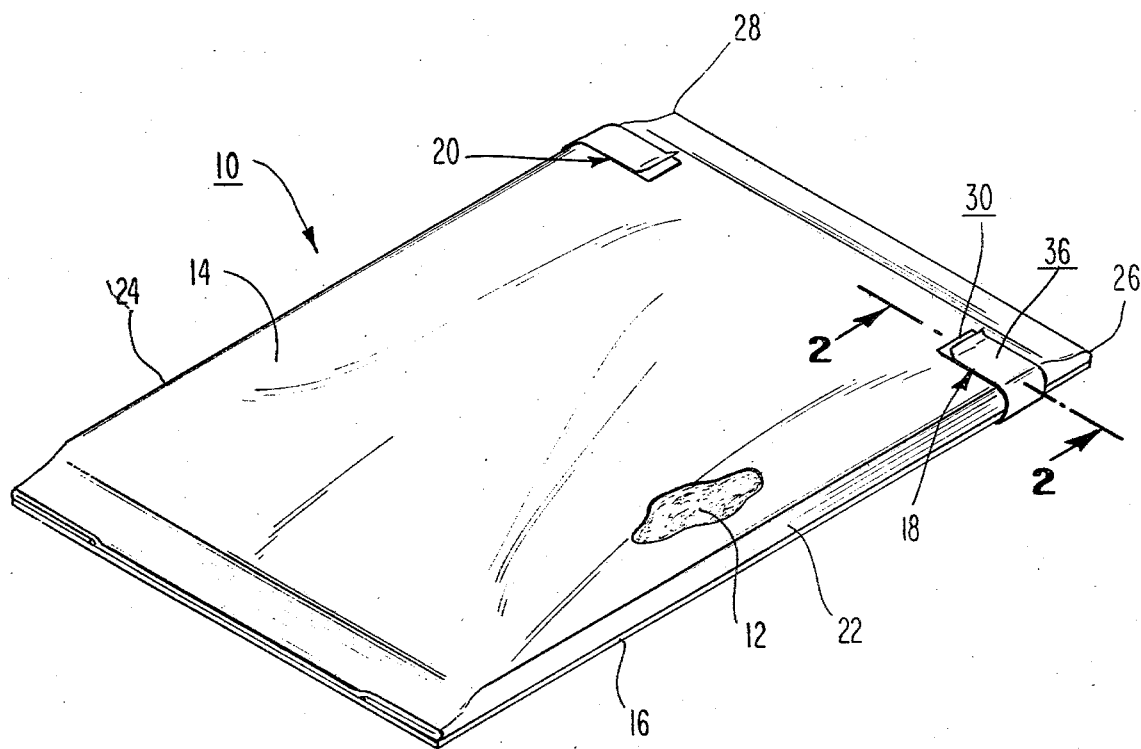
FIG. 1 is an isometric view of a disposable diaper including a unique fastener tape system in accordance with this invention.

In the embodiment shown for illustration in FIG. 1, a disposable diaper 10 includes an absorbent core 12 disposed between a moisture-pervious facing sheet 14 and a moisture-impervious backing sheet 16, such as a thin polyolefin sheet approximately 0.001 inches thick. The moisture-pervious facing sheet can be of any desired construction which will permit urine to pass rapidly through it. Carded webs of rayon fibers and polyester fibers have been employed satisfactorily as such facing sheets. A common absorbent core 12 is a loosely compacted batt of wood pulp fibers formed from pulp lap sheets by a fiberizing operation. However, other absorbent structures, such as multiple plies of crepe wadding, can be employed as the absorbent core.

Figure 2:
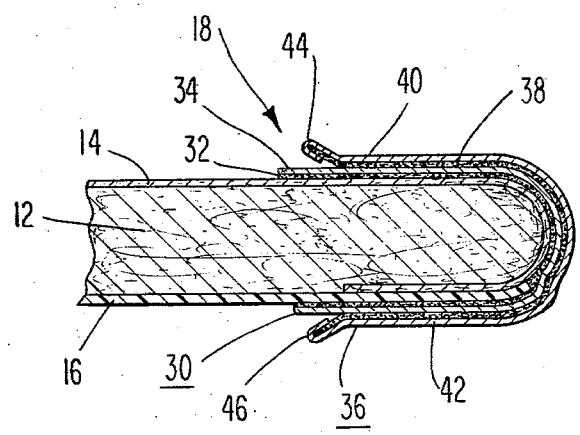
FIG. 2 is a sectional view along line 2—2 of FIG. 1.

Referring to FIGS. 1 and 2, fastener tape systems 18 and 20 are adhered to segments of the disposable diaper 10 adjacent logitudinal side edges 22 and 24, respectively. These systems 18 and 20 are identical in construction, and are adhered adjacent rear corners 26 and 28 of the diaper 10 as is well known in the art. In view of the fact that the fastener tape systems are of an identical construction, only the tape system 18 will be described herein.

Referring to FIG. 2, the fastener tape system 18 includes a release strip 30 folded about the logitudinal side edge 22 of the diaper. An adhesive layer 32 is included on one side of the release strip for positively securing the release strip to both the moisture-pervious facing sheet 14 and the opposed backing sheet 16. The surface of release strip 30 opposite adhesive layer 32 constitutes a release surface 34. Release strips of the type identified at 30 are extremely well known in the prior art, and are disclosed in many patents directed to disposable diapers. For example, release strips employed in the disposable diaper field are disclosed in the following U.S. Pat. Nos. 3,630,201 (Endres); 3,776,234 (Hoey); 3,794,038 (Buell); 3,797,495 (Schmidt); 3,848,594 (Buell); 3,848,596 (Pennau); 3,893,460 (Karami); 3,920,016 (Mesek); 3,926,191 (Tritsch) and 3,931,666 (Karami).

Referring again to FIG. 2, the fastener tape system 18 also includes an adhesive tape fastener 36. The tape fastener 36 is in the form of a strip having a pressure-sensitive adhesive layer 38 on one side thereof. The fastener is folded about the longitudinal side edge 22 of the diaper to provide a first tape section 40 overlying the facing sheet 14 and a second tape section 42 overlying the backing sheet 16. The adhesive associated with the first and second tape sections 40 and 42 face toward the diaper and are adhered to the release surface 34 of the release strip 30. Preferably the free ends of the first and second tape sections 40 and 42 are folded over to form adhesive-free gripping tabs 44 and 46, respectively. These tabs remain separated from the release surface 34, and provide a convenient gripping region by which a person can peel tape sections 40 and 42 from their engagement with the release surface 34.

The adhesive tape fastener 36 can be formed from any conventional substrate normally employed in forming pressure-sensitive adhesive tapes for use in the disposable diaper field. For example, the adhesive tape fastener 36 can be formed from paper, plastic, foil, and other suitable materials.

Referring to FIGS. 3-5, the manner in which the fastener tape system 18 is employed will now be described. It should be understood that the fastener tape systems 18 and 20 are employed in an identical manner, and therefore, the description which follows will be limited to the operation of the system 18. Referring to FIG. 3, the first tape section 40 is gripped by its end tab 44 and peeled off of the release surface 34. This first tape section is then adhered to the backing sheet 16, after the diaper has been positioned about the torso of a wearer, to secure the diaper on the wearer (FIGS. 3 and 4). When the first tape section 40 is adhered to the backing sheet 16, as described above, it becomes firmly affixed to said backing sheet to form a permanently anchored end for the adhesive tape fastener 36. That is, the first tape section 40 is no longer considered to be a removable section for permitting the diaper 10 to be opened for inspection and/or adjustment. However, as can be seen in FIG. 3, the second tape section 42 is adhered to the release surface 34, and can be gripped by its adhesive free tab 46 to be peeled therefrom. In this regard it is important that the release surface 34 of the release strip 30 have a limited affinity in peel for the adhesive layer 38 of the second tape section 42. It is also important that the adherence in shear between the release surface 34 of strip 30 and the adhesive layer 38 of the second tape section 42 be sufficient for retaining the second tape section 42 on the release surface 34 during the normal body movements of a wearer. When it is desired to inspect the interior of the diaper 10 and/or readjust the diaper about the torso of a wearer, the second tape section 42 is peeled off of the release surface 34, as shown in FIG. 5. Thereafter, the diaper can either be disposed of, in the event that the examination of the interior indicates it is excessively soiled, or the diaper can be refastened about the torso of a wearer by adhering the second tape section 42, through its adhesive layer 38, either back on the release surface 34, or on the backing sheet 16 adjacent said release surface.

The particular release surface 34 and adhesive layer 38 which can be employed in the fastener tape system 10 can be determined empirically based on the criteria stated in the preceding paragraph. Desirably, the peel strength between the release surface 34 and the adhesive layer 38 should be maintained below 1 lb/in. Desirably, the shear strength between these surfaces should be maintained above 15 lbs/in$^2$, and most preferably above 29 lbs/in$^2$.

The peel strength is calculated by the Quick Stick test described in PSTC-5, Revision 11/70, of the Pressure Sensitive Tape Council. This test has been modified by replacing the standard surface with the release surface employed in combination with the adhesive layer in the fastener tape systems of this invention.

The shear strength is determined by the following procedure:
first, the release liner 13 is adhered through its adhesive layer to a stainless steel plate;
second, a test tape sample, 1 inch wide by 6 inches long, is adhered through its adhesive surface to the release surface of the liner over a 1 square inch area, and with a section of the tape extending beyond the plate for gripping in a jaw of an Instron tensile tester;
third, the sample is pressed against the release liner on the stainless steel plate by a 4 ½ pound rubber roller, once in the 6 inch direction and once in the 1 direction of the tape;
fourth, a portion of the plate is gripped by the top jaw of the Instron, the exposed section of the test sample is gripped by the bottom jaw, and the jaws are separated at a speed of 0.5 inches/minute; and
fifth, the forth required to separate the first sample from the release liner is recorded in lbs./in$^2$.

In a representative embodiment of this invention the release strip 30 can be brand 3M(Y2621), sold by Minnesota Mining and Manufacturing Co. of St. Paul, Minnesota. A tape fastener 36 which has been found to be compatible with the above release strip 30 is Fasson JCS-1, a Tyvek-backed tape sold by the Industrial Division of Fasson in Painesville, Ohio.

Different modifications can be employed within the scope of this invention. For example the release surface engaging the adhesive layer of the first tape section 40 can be different from the release surface engaging the adhesive layer of the second tape section 42 to provide different peel and/or shear characteristics, as desired. It is also within the scope of this invention to provide the release surface 34 with a limited area, or areas, that either are free of a release agent or include an adhesive agent to insure that the tape fastener 36 does not become separated from the release strip 30 either prior to or during use of the fastener tape system 10.

Referring to FIG. 6, a second embodiment of a fastener tape system is indicated at 18A. The tape system 18A includes a fixed strip 30A and a movable tape fastener 36A. The fixed strip 30A includes a release surface 34A overlying the facing sheet 14 and facing outwardly thereof. The fixed strip 30A differs from the release strip 30 in that it includes an adhesive layer 34B, rather than a release surface, overlying and facing outwardly from the backing sheet 16 of the diaper.

The movable tape fastener 36A includes an adhesive layer 38A as part of a first tape section 40A. The first tape section 40A is shown in its position for initially securing the diaper about the torso of a wearer. However, in its packaged condition the first tape section 40A is adhered to the release surface 34A in overlying relationship with the facing sheet 14. The tape fastener 36A differs from the tape fastener 36 in that a second tape section 42A thereof includes a release surface 38B, instead of an adhesive layer. The tape fastener 36A includes adhesive free end tabs 44A and 46A associated with the first and second tape sections 40A and 42A, respectively. These adhesive free end tabs permit easy gripping of the tape sections 40A and 42A to permit them to be peeled off of the cooperating surfaces of the fixed strip 30A.

The fastener tape system 18A is initially employed to fasten a diaper about the torso of a wearer in the same manner as the fastener tape system 18 described earlier. Specifically, the first tape section 40A is gripped by its end tab 44A and peeled off of the release surface 34A to the position shown in FIG. 6. This first tape section is then adhered to the backing sheet 16 to secure the diaper on the wearer in a manner similar to that shown in FIGS. 3 and 4. When the first tape section 40A is adhered to the backing sheet 16, as described above, it becomes firmly affixed to said backing sheet to form a permanently anchored end for the tape fastener 36A. However, the second tape section 42A includes an inwardly directed release surface 38B adhered to adhesive layer 34B of the fixed strip 30A. This permits the second tape section 42A to be easily peeled from the adhesive layer 34B to permit inspection of the interior of the diaper. Thereafter, the diaper can either be disposed of, in the event that the examination of the interior indicates the diaper is excessively soiled, or the diaper can be refastened about the torso of a wearer by adhering the second tape section 42A back into overlying relationship with the adhesive layer 34B. Preferably the second tape section 42A has a greater width and length than the adhesive layer 34B to insure that the adhesive layer always remains completely covered by the second tape section 42A. If the adhesive layer 34B is not completely covered by the tape section 42A it will be exposed to adhere to outer garments of the wearer, and this may be undesirable.

The modifications described earlier in connection with the fastener tape system 18 can also be employed in connection with the fastener tape system 18A. In addition, the adhesive layer 38A associated with the movable tape fastener 36A can be designed to overlap, and adhere to the adhesive layer 34B associated with the fixed strip 30A. In this manner adhesive-to-adhesive engagement is maintained between the movable tape fastener 36A and the fixed strip 30A to positively retain the tape fastener on the fixed strip. When the adhesive layers 38A and 34B are adhered to each other it may not be required to establish a high shear strength between the adhesive layer 34B of the fixed strip 30A and the release surface 38B of the movable fastener 36A in order to retain the second tape section 42A connected to the disposable diaper to permit the tape fastener to perform its intended fastening function.

Having described my invention I claim:

1. A method of manipulating a disposable diaper, said diaper having front and back surfaces adapted to face toward and away from a wearer, respectively, when said diaper is placed on the wearer, said diaper including an adhesive tape fastener folded about a side edge of one segment of the diaper to provide a first tape section overlying the front surface of said one diaper segment and a second tape section overlying the back surface of said one diaper segment, said first tape section including an inwardly facing adhesive layer adhered to the front surface of said one diaper segment through an outwardly facing release surface and said second tape section being attached to the back surface of said one diaper segment through the cooperation of a release surface and an adhesive layer, said method including the steps of:

a. placing the diaper about the torso of a wearer with the front surface facing the wearer and end regions encircling the waist region of said wearer to bring a second segment of the diaper adjacent said one segment;

b. separating the first tape section from its release surface on the one diaper segment to expose the adhesive layer thereon and adhering the first tape section, through its exposed adhesive layer, to the back surface of the second diaper segment for initially retaining the diaper about the torso of the wearer, and, when the diaper is to be opened;

c. separating the second tape section from the back of the one diaper segment at an interface between the release surface and the adhesive layer that cooperate to attach the second tape section to the back surface of said one diaper segment.

2. The method according to claim 1, including the step of adjusting the diaper to improve its fit on the wearer after the second tape section has been separated from the back of the one diaper segment, and thereafter, reattaching the second tape section to the one diaper segment for maintaing said diaper in its adjusted position.

3. A method of manipulating a garment having segments to be connected together, an adhesive tape fastener having two tape sections at opposed ends thereof, one of said tape section being connected to a first segment through an adhesive surface-release surface interface and the other of said tape sections being positionable beyond an edge of the first segment and including an adhesive layer for attachment to a second segment, said method including the steps of:
- attaching the other tape section to the second segment to connect said first and second segments together, and, when these segments are to be unconnected;
- separating said one tape section from the first segment at the adhesive surface-release surface interface.

4. The method of claim 3 including the additional step of reattaching said one tape section to the first segment.

* * * * *